United States Patent [19]

Daly

[11] Patent Number: 4,773,403

[45] Date of Patent: Sep. 27, 1988

[54] PENILE PROSTHESIS

[75] Inventor: Mark D. Daly, Milwaukee, Wis.

[73] Assignee: Medical Engineering Corporation, Racine, Wis.

[21] Appl. No.: 86,066

[22] Filed: Aug. 17, 1987

[51] Int. Cl.⁴ .............................................. A61F 2/26
[52] U.S. Cl. ............................................................ 128/79
[58] Field of Search ........................................... 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,204,530 | 5/1980 | Finey | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,449,520 | 5/1984 | Palomar et al. | 128/79 |
| 4,550,719 | 11/1985 | Finney et al. | 128/79 |
| 4,550,720 | 11/1985 | Trick | 128/79 |
| 4,572,168 | 2/1986 | Fischell | 128/79 |
| 4,573,985 | 3/1986 | Finney | 604/349 |
| 4,574,792 | 3/1986 | Trick | 128/79 |
| 4,590,927 | 5/1986 | Porter et al. | 128/79 |
| 4,594,997 | 6/1986 | Hakky | 128/79 |
| 4,596,242 | 6/1986 | Fischell | 128/79 |
| 4,611,584 | 9/1986 | Finney | 128/79 |
| 4,622,958 | 11/1986 | Finney | 128/79 |

FOREIGN PATENT DOCUMENTS

WO80/00302 3/1980 PCT Int'l Appl. .

Primary Examiner—John J. Wilson
Assistant Examiner—Cary E. Stone
Attorney, Agent, or Firm—Quarles & Brady

[57] ABSTRACT

An improved penile prosthesis to be surgically implanted in man for the treatment of erectile impotence includes at least one elongated, flexible cylinder containing therein a hydraulic system comprising a pressure chamber, a reservoir and a pump. It also includes an outer girth adjusting chamber concentric with the pressure chamber. The girth adjusting chamber is connected by tubing to a pressure bulb located outside the cylinder so that the girth adjusting chamber can be inflated and the girth of a penis increased by transferring fluid from the pressure bulb to the adjusting chamber.

6 Claims, 3 Drawing Sheets

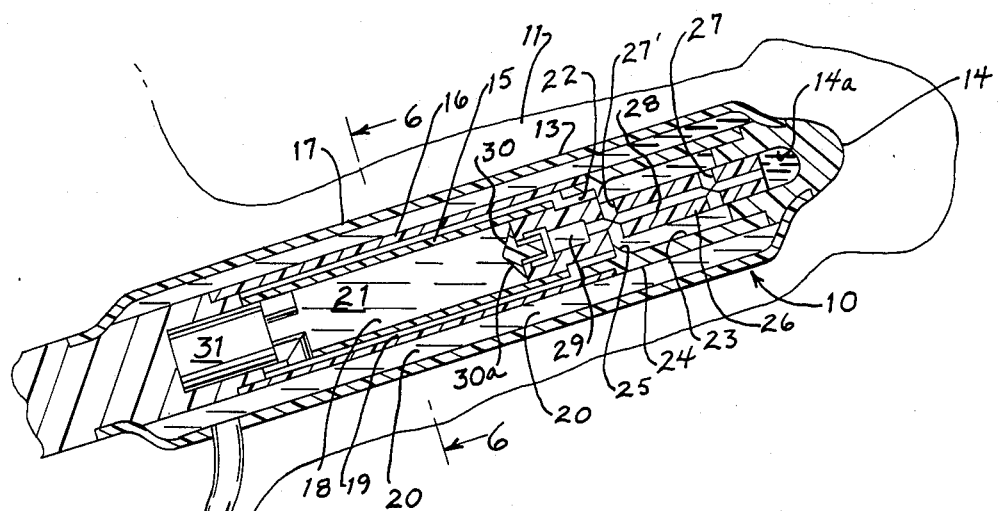
FIG. 5
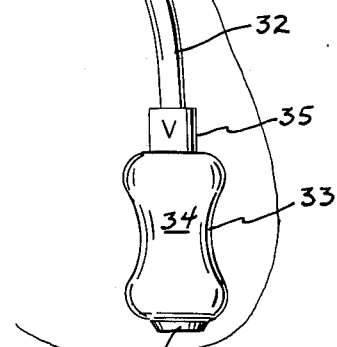
FIG. 6
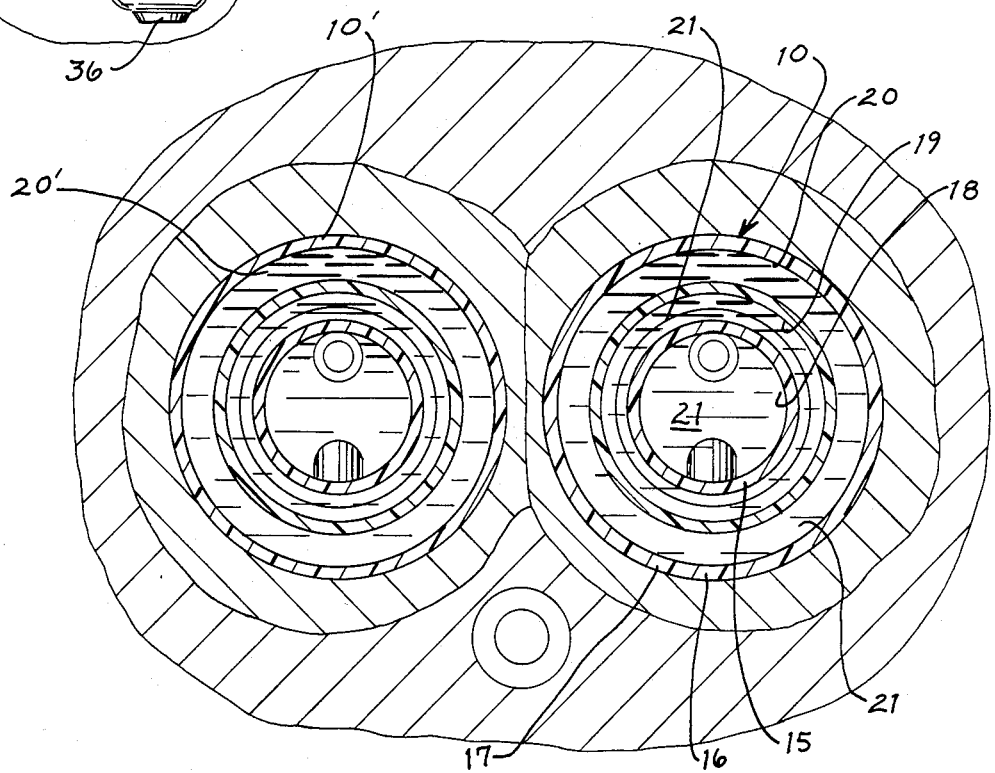

PENILE PROSTHESIS

RELATED APPLICATION

This application is related to the copending, commonly owned U. S. Patent application Ser. No. 887,069 filed July 17, 1986.

FIELD OF THE INVENTION

The present invention relates to penile prostheses for curing erectile impotence. More particularly, it relates to an inflatable penile prosthesis.

BACKGROUND OF THE INVENTION

In some instances of erectile impotence in which the patient does not respond to more conventional therapy, the surgical implanting of a penile prosthesis may be the only practical means of remedying the impotency.

In the past, several types of penile prostheses have been employed. The first type is a pair of rods of suitable stiffness each of which is surgically implanted into a corpus cavernosum of the penis. One disadvantage of the rod-type implant is that the stiffness of the rods makes it difficult to implant rods of sufficient diameter in a flaccid penis so that the penis in the erectile state will have a normal girth. The sleeve prosthesis disclosed in U.S. Pat. No. 4,204,350 is an attempt to overcome that disadvantage.

The other type of penile prosthesis which is available is the inflatable prosthesis. The most common inflatable prosthesis includes two fairly long, inflatable, distensible tubes that are surgically implanted in the corpora cavernosa of the penis. Each of the two tubes is connected by tubing to a pressure bulb of inflating fluid which is implanted elsewhere in the body. The distensible tubes are collapsible so that they can be easily implanted and they can be inflated to increase the girth of the penis to that attained in a normal erection. However, because of the large volume required to pressurize and rigidize the inflatable tubes, the pressure bulbs can be relatively large. In the prosthesis of U.S. Pat. No. 3,954,102, the pressure bulbs are relatively small but there is a single relatively large reservoir which is implanted in the abdominal cavity.

Another type of inflatable penile prosthesis that can result in increased girth is that of U.S. Pat. No. 4,009,711. It comprises two implants each having its own relatively large, pressurizing bulb which is surgically implanted in the scrotal sac. Each implant includes a non-distensible stem made of a relatively stiff material to support the implant and an integral, collapsible, balloon-like distensible portion which is implanted into the corpora of the pendulous penis and inflated with the pressure bulb to affect an erection.

Still another type of penile prosthesis that can be used to increase girth is that disclosed in U.S. Pat. No. 4,201,202. It is a combination of a rod-type implant with an inflatable sleeve which is attached about the rod to form an inflatable chamber. A pressure bulb is connected to the chamber by tubing for inflating the chamber.

In Finney U.S. Pat. No. 4,573,985 an implant is disclosed which is implanted to increase the girth of a flaccid penis so that it will retain a urinary collection device. The implant is provided with a wall of resealable material so that fluid can be introduced into the implant with a cannula.

Recently, several inflatable penile prostheses for curing impotency have become commercially available which can be implanted completely in the penis. The prostheses basically comprise a pair of cylindrical implants each containing a pump, a reservoir and a pressure chamber. The pressure chambers are non-distensible so that only small amounts of fluid are needed to be transferred from the reservoirs to make them rigid. These inflatable prostheses provide many advantages over prior art implants, but they do not increase the girth of the penis. Representative of such prostheses are those shown in U.S. Pat. Nos. 4,399,811 and 4,590,927.

It obviously would be desirable to have a penile prosthesis in which the girth of the penis could be increased and preferably adjusted.

SUMMARY OF THE INVENTION

It is the general object of the present invention to disclose an improved penile prosthesis with means for increasing the girth of the penis.

It also is an object to disclose an implant in which the penile girth can be variably adjusted.

The present invention is a penile prosthesis comprising a pair of elongated, flexible, cylindrical implants each containing a pressure chamber, a reservoir for pressurizing fluid and a pump for transferring fluid from the reservoir to the pressure chamber. The prosthesis of the present invention differs from prior art devices in that each implant also has a separate, inflatable, outer cylindrical chamber positioned radially about the pressure chamber, inflation means for inflating the outer chamber to increase penile girth and a valve for controlling the flow of the pressurizing fluid between the inflation and the inflatable outer chamber. The means for inflating the outer chambers can be a single pressure bulb in the scrotal sac connected by tubing to the outer chambers. The implant also may contain a septum or self-sealing valve so that additional fluid can be added to the bulb or outer chamber.

In a preferred embodiment, the implants of the prosthesis each have a relatively stiff, proximal end which is to be implanted into the root end of the corpus cavernosum to anchor and support the implant and a flexible distal portion which includes the pressure chamber and outer chamber which is to be implanted into the portion of a corpus cavernosum in the pendulous penis. A single pressure bulb which can be implanted in the scrotal sac is connected to the outer chambers of both implants by tubing.

The penile prosthesis of the present invention provides a distinct advantage over previously available prostheses because it permits the penile girth to be increased and variably adjusted.

The prothesis of the present invention is preferrably implanted with the pressure chambers unpressurized and the outer chambers containing only a small amount of fluid to prevent the walls from sticking to each other. After the patient has completely healed the non-distensible pressure chambers are pressurized to effect an erection, and, if the girth of the penis is smaller than desired, the penile girth is then effectively increased by transferring liquid from the pressure bulb to the inflatable outer chambers. This is done by simply squeezing on the pressure bulb which opens the valve and permits the fluid to enter and inflate the outer chambers.

BRIEF DESCRIPTION OF THE DRAWINGS

FIG. 5 is a view similar to FIG. 3 but showing the outer chamber inflated to increase girth; and, FIG. 6 is a view taken along line 6—6 in FIG. 5.

DESCRIPTION OF THE PREFERRED EMBODIMENT

Figure 1:
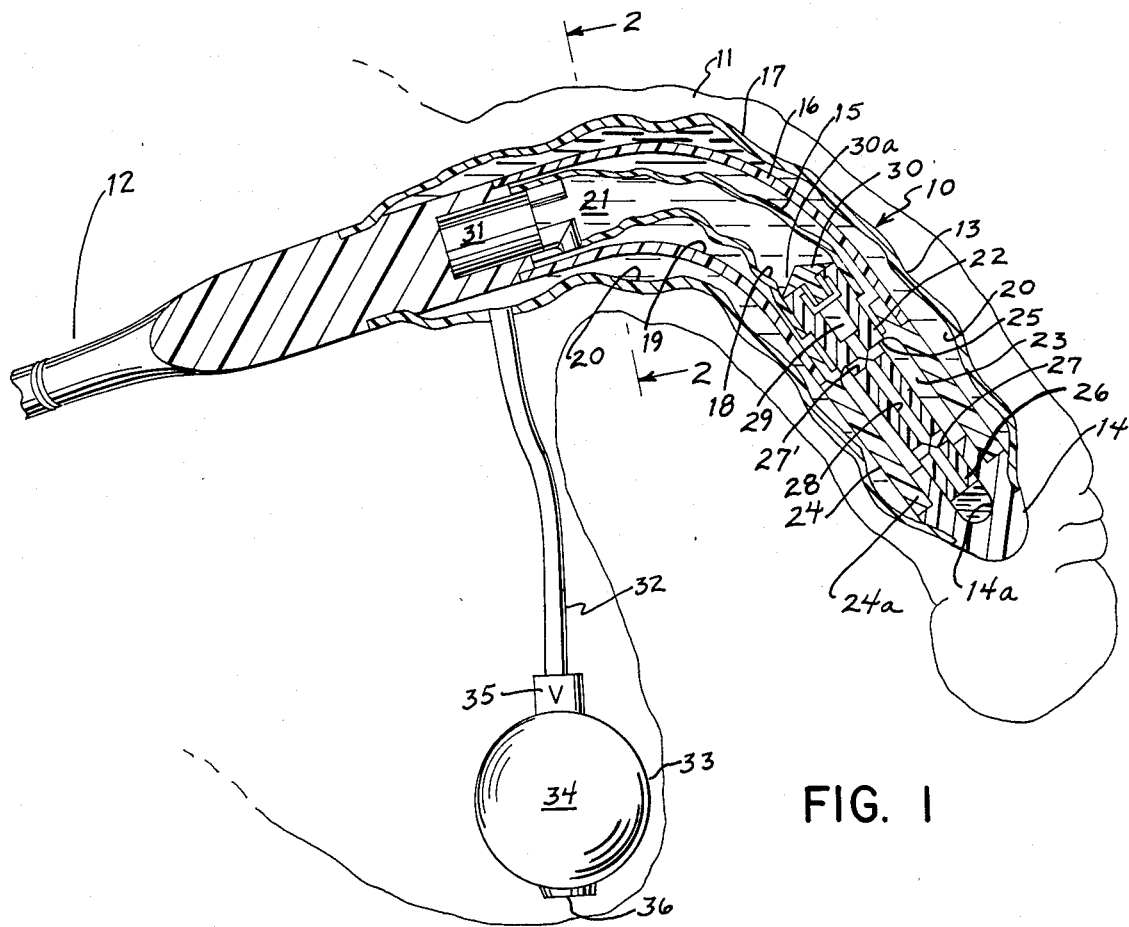
FIG. 1 is a sectional view of a penis with a penile implant of the prosthesis of the present invention in a depressurized condition with the outer chamber uninflated.

In the drawings, a penile prosthesis is shown which is comprised of two identical implants 10 and 10'. The implants 10 and 10' identical; therefore, only implant 10 will be described.

Figure 2:
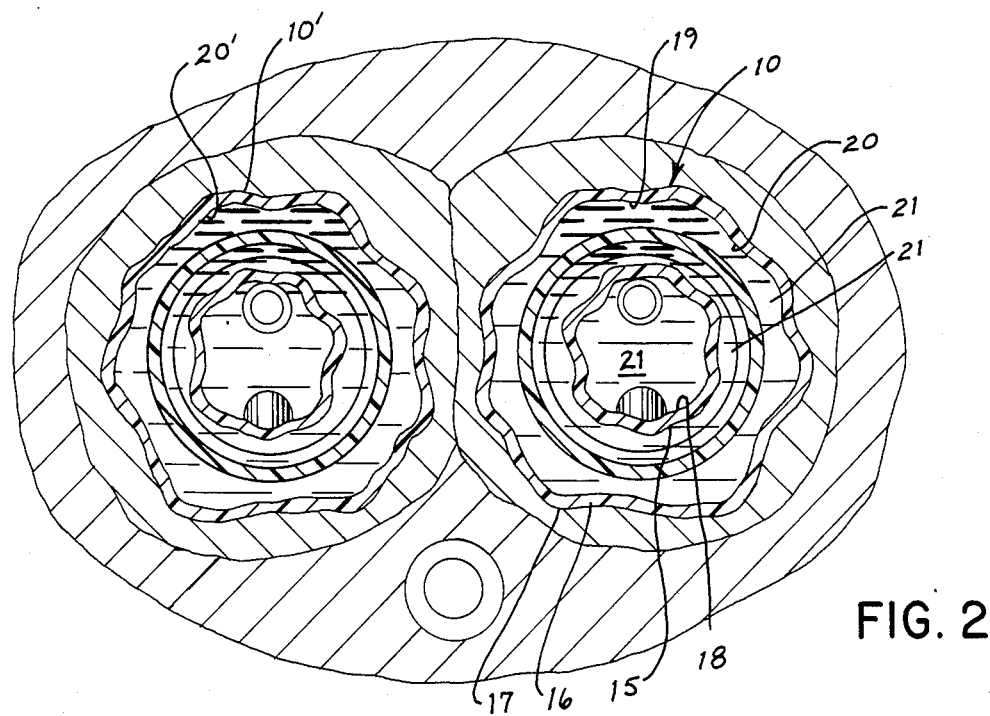
FIG. 2 is a cross sectional view taken along the lines 2—2 in FIG. 1.
Figure 4:
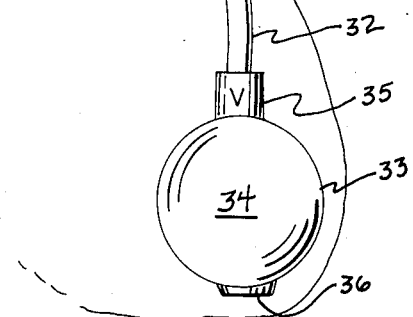
FIG. 4 is a view taken along line 4—4 in FIG. 3.
Figure 4:
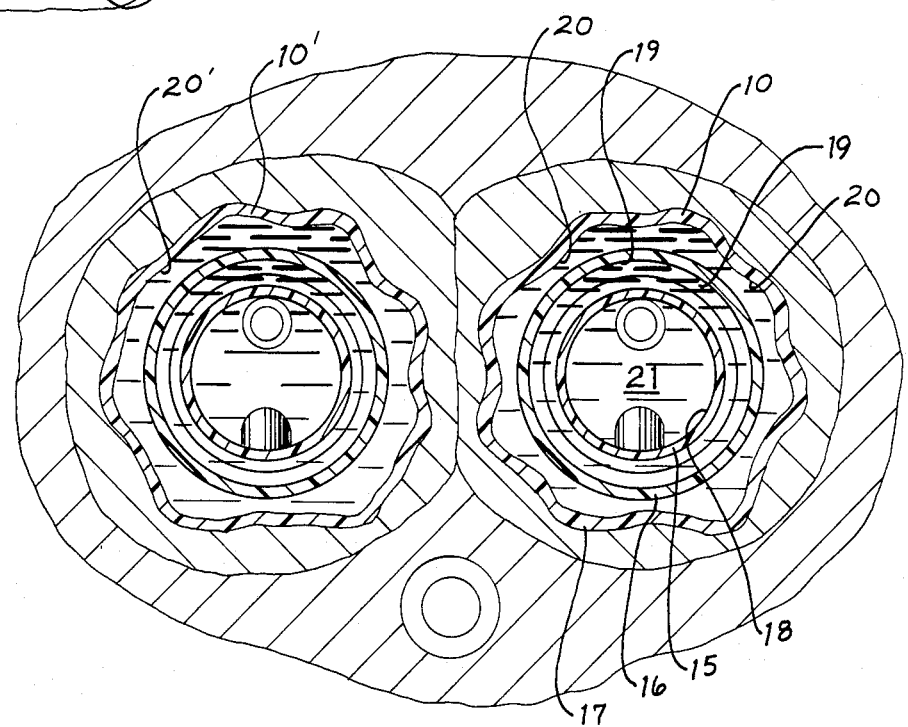

The implant 10 comprises an elongated cylindrical member 11 with a short, proximal stem 12 of relatively stiff material which is implanted in the root end of a corpus cavernosum to support and anchor the implant, and a longer distal portion 13 which is of a softer, more flexible material which is implanted into the portion of the corpus cavernosum in the pendulous penis. The distal portion 13 is provided with a tip 14 which is paraboloidal in shape to conform to the inner shape of the end of the corpus cavernosum. As seen in FIGS. 2, 4, and 6, each of the implants 10, 10' is positioned in a separate corpus cavernosum of the penis.

The distal portion 13 of the implant 10 includes the concentric cylindrical sleeves 15, 16 and 17 which are each attached in a fluid tight manner to the stem 12 and to the tip 14 to form three concentric chambers 18, 19 and 20, respectively. The sleeve 15 which forms the wall of the pressure chamber 18 is of a relatively inelastic material, such as a silicone coated mesh or woven fabric, so that the chamber 18 is non-distensible even when pressurized. The sleeve 15 cooperates with the sleeve 16 which is spaced outwardly from the sleeve 15 to form the reservoir chamber 19.

The sleeves 16 and 17 may be made of a distensible material, such as nonreinforced silicone rubber. The sleeve 16 also cooperates with the sleeve 17 to form the outer girth adjusting chamber 20. The necessary fluid tight seals between the sleeves 15, 16 and 17 and the stem 12 and tip 14 may be made with a suitable adhesive or by other suitable means.

Prior to discussing the girth adjusting improvement which constitutes the present invention, the pressurization and depressurization of the implant 10 will be described.

Figure 3:
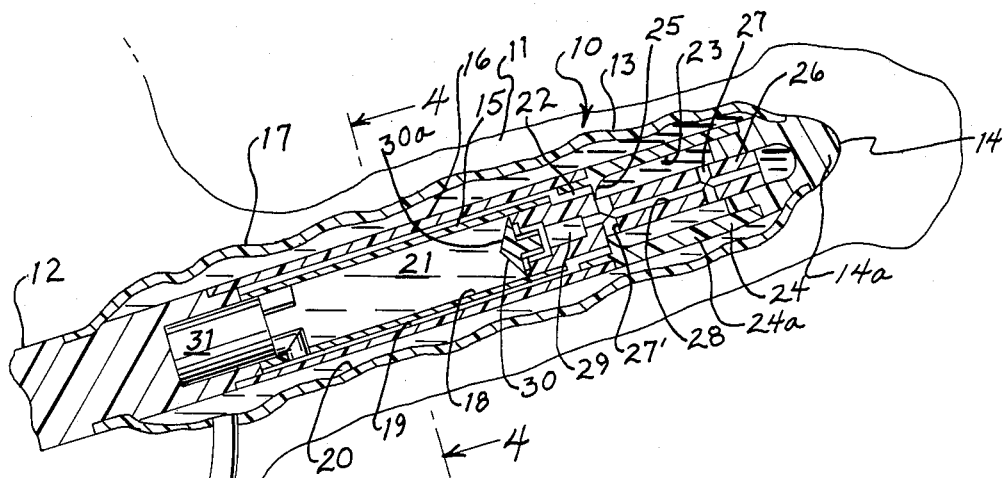
FIG. 3 is a view similar to FIG. 1, except the pressure chamber is fully pressurized.

As seen in FIGS. 1 and 3, the implant 10 is in a non-pressurized state and both the chambers 18 and 19 are substantially filled with a non-compressible hydraulic fluid 21 which may be a biocompatible fluid such as saline or a free flowing silicone gel. In these views, the outer chamber 20 contains a small amount of fluid 21 to prevent the chamber walls from sticking to each other.

In the non-pressurized state, the soft, flexible, distal portion 13 of the implant 10 flexes and permits the penis to assume a substantially normal, flaccid position as seen in FIG. 1. However, when the implant 10 is in the pressurized state, as seen in FIGS. 3 and 4, the distal portion 13 is rigid as the result of the non-distensible inner chamber 18 being completely filled with fluid under pressure and the penis assumes an erectile position.

As seen best in FIGS. 1, 3 and 5, there is a passage 22 in the portion adjacent the tip 14 which leads from the reservoir chamber 18 to a pumping chamber 23 of a pump 24. As seen therein the exit of the passage 22 is closed by a one way flap valve 25 which only opens when the fluid pressure in the passage 22 exceeds that in the pumping chamber 23.

Positioned within the pumping chamber 23 is a support member 26 which has axial passages 27, 27' and a longitudinal passage 28 extending therethrough. The support member 26 extends from and provides communication between the hollow interior 14a of the conical tip 14, the pumping chamber 23 and the pressure chamber 18. The end of the passage 28 opposite the conical tip 14 has an enlarged exit 29 in which there is positioned an umbrella type flexible check valve 30. The check valve 30 is normally kept seated closing the passage 28 by fluid pressure in chamber 18. However, when the wall of the pump 24 is squeezed the fluid pressure in the pumping chamber 23 and passage 28 exceeds that in pressure chamber 18 and the edges of the check valve 30 are deflected allowing fluid 21 to flow about the check valve 30 into chamber 18.

The implant 11 is pressurized by sequentially squeezing the resilient wall 24a of the pump 24 to force the hydraulic fluid 21 from the pumping chamber 23 into non-distensible pressure chamber 18 under pressure and then allowing the wall 24a to assume its normal shape. When the pump wall 24a is first squeezed the fluid 21 originally in the pumping chamber 23 is forced through the axial passages 27, and longitudinal passage 28 out the exit 29 forcing the edges of the check valve 30 off their seat allowing the fluid 21 to flow about the valve 30 into the pressure chamber 18. The increased pressure in the pumping chamber 23 keeps the flap valve 25 seated closing passage 22 and preventing flow into reservoir chamber 19. Thereafter, when the wall 24a is allowed to assume its normal position, a reduced pressure is formed in the pumping chamber 23 and as a result the flap valve 25 is moved off its seat allowing fluid 20 to flow from the reservoir chamber 19 into the pumping chamber 23. Whenever the pressure in pumping chamber 23 equals or exceeds that in reservoir chamber 19 the flap valve 25 is seated closing the passage 22.

When the pressure chamber 18 is sufficiently pressurized and rigid, the pumping is stopped whereby the exit 29 of the passage 28 is closed by pressure of the fluid 21 in pressure chamber 18 upon the outer surface 30a on the enlarged head of the check valve 30. As a result, the pressure chamber 18 remains filled, pressurized and rigid, as seen in FIG. 3, until the pressure control valve 31 is opened to allow fluid 21 to flow back to the reservoir chamber 19 whereupon the implant 10 resumes the non-pressurized state seen in FIG. 1.

If desired, the filling and pressurizing of the non-distensible pressure chamber 18 may be facilitated by manually squeezing the penis to help force fluid 21 which is in reservoir chamber 19 through the passage 22, past the flap valve 25 and into the pumping chamber 23.

It will be appreciated that a variety of pump mechanisms other than that shown can be used. However, the pump should be of the type which opens when it is squeezed and automatically closes when the squeezing stops.

The preferred pressure control valve 31 may be manually opened and will automatically open when the pressure in the pressure chamber 18 exceeds a predetermined level.

Referring now to FIGS. 1, 4 and 6, the improvement which constitutes the present invention will be described. As seen therein, the third concentric or adjusting chamber 20 is connected by a length of tubing 32 to a pressure bulb assembly 33 which is implanted in the scrotal sac. A similar length of tubing (not shown) connects the adjusting chamber 20' of the other implant 10' to the pressure bulb assembly 33.

The pressure bulb assembly 33 includes a pressure bulb 34 and a valve 35 for controlling the flow of pressurizing fluid 21 between the pressure bulb 34 and the chamber 20. The valve 35 is normally closed but it can be either opened automatically by squeezing the pressure bulb 34 or by manually deforming the housing of the valve 35. The valve 35 is of the type which normally closes when the squeezing pressure on the bulb 34 stops. Suitable valves are known and disclosed in U.S. Pat. No. 4,060,080.

The implant can be returned to the flaccid stage by squeezing the pressure chamber 18 which causes the pressure relief valve 31 to open and the fluid 21 to leave the pressure chamber 18 and return to the reservoir chamber 19.

Referring now to FIGS. 5 and 6 the method for increasing penile girth will be described. If it is desired to increase penile girth the pressure bulb 34 is squeezed whereupon the valve 35 opens and pressurizing fluid 21 flows from the bulb 34 via the tubing 32 into the adjusting chamber 20 causing it to expand outwardly and increase penile girth. The girth increasing fluid 21 in the adjusting chamber 20 can be left in the chamber 20 when the pressure chamber 18 is depressurized or transferred back to the pressure bulb 34 by opening the valve 35 by manually deforming it while squeezing the girth adjusting chamber 20.

The pressure bulb 34 which is of flexible resilient material is provided with a septum or one-way valve 36, so that additional fluid can be added to the pressure bulb 34 with a hypodermic needle (not shown) even after the implant 10 has been implanted. This may be necessary where the amount of fluid which can be transferred to increase the girth to the desired level by squeezing the normally filled pressure bulb 34 is insufficient.

The proximal stem 12 of the penile implant 10 is anchored in the root end of the corpus cavernosum, and the paraboloidal tip 14 is positioned in the glans end of the corpus cavernosum. As a result, the implant 10 is positioned correctly in the corpus cavernosum of the penis and the likelihood of displacement is minimized.

In the preferred embodiment of the invention, the proximal stem 12 of the member 11 has a Shore hardness of about 70, and the material has sufficient tensile strength for its intended use. Although a material of the described characteristics is preferred, any material which performs satisfactorily under conditions of use can be employed.

The sleeve 15 is preferably made of a silicone elastomer coated woven or knit fabric which provides to a limited predetermined expansion to allow the penis to become longer and to contain the pressure so that the tunica albuginea will not distend. Alternatively, the sleeve 15 also can be made of a material which does not distend either axially or longitudinally.

The diameter of the sleeve 15 is sufficient to form a functional pressure chamber 18. The use of a sleeve material which does not distend or distends only to a limited extent makes it possible to raise the fluid pressure in the chamber 18 to the desired high level with only a minimum of pressurizing fluid. The sleeve may be made of unreinforced silicone rubber or any functionally equivalent or superior material. The sleeves 16 and 17 are preferrably distensible or of limited distensibility and can be made of silicone rubber or similar elastomer.

The preferred method of implantation of the implants is through the perineum. After appropriate incision, the corpus cavernosum is dilated distally and proximally to accept the implant. The approximate anatomical measurements are made to ensure that the stem of the implant will be positioned at the base of the penis below the pelvic bone. An implant having an appropriately sized distal portion is selected. The proximal stem of the implant is then cut to the appropriate length, if necessary. During the manufacture of the implant the length of proximal stem may be deliberately made longer than necessary thereby permitting it to be trimmed to the correct length at the time of surgery. Only one implant of each distal portion length need, therefore, be available since other anatomical size variations may be accommodated by trimming the proximal stem. This greatly reduces the number of implant sizes which must be produced over that which would be required if no such size alteration were possible.

The proximal stem is inserted in the dilated crus after trimming. The identical procedure is performed on the other side of the penis to complete the surgical procedure. The incisions are then closed. The stems of the two implants may diverge laterally to accommodate the anatomy and provide lateral stability to the penis.

In the preferred embodiment, all the parts and components of the prosthesis are made of medical application silicone rubber which is non-reactive, non-toxic and well tolerated by the adjacent organic tissues. Silicone rubber is preferred because it is quite resistant to wear and tear and remains functional for long periods of time. However, other suitable materials may be employed, if desired.

The foregoing description has been for purposes of illustration only. For example, the improvement which constitutes the present invention could be used with other types of inflatable implants than that described including implants with a rear or front reservoir in place of a reservoir concentric with the pressure chamber. Furthermore, although the use of a common pressure bulb for the adjusting chambers of two cylinders has been described, one pressure bulb could be employed for each girth adjusting chamber. Therefore, it will be readily apparent to those skilled in the art to which this invention relates that a variety of changes and modifications might be made without departing from the spirit and scope of the invention.

I claim:

1. In a penile prosthesis comprising: at least one elongated, flexible cylindrical member adapted to be implanted in the corpus cavernosum of the pendulous penis, said member containing a non-distensible inner pressure chamber, a reservoir, a passage connecting the pressure chamber and the reservoir and a pump for transferring fluid from the reservoir to the pressure chamber; the improvement comprising an inflatable girth adjusting chamber concentric with and radially outside the pressure chamber, inflating means located outside the member for delivering expanding fluid to said adjusting chamber, and means connecting the adjusting chamber and the inflating means so that fluid can be introduced into the adjusting chamber to inflate said chamber and increase the girth of a penis in which said prosthesis is implanted.

2. A penile prosthesis of claim 1 in which the inflating means is a pressure bulb.

3. A penile prosthesis of claim 2 which includes valve means for controlling flow between the pressure bulb and the adjusting chamber.

4. The implant of claim 3 in which the valve means opens automatically when the pressure bulb is squeezed to permit flow from the bulb to the adjusting chamber, said valve means being operable from the outside to permit fluid to flow from the adjusting chamber back to the pressure bulb.

5. The prosthesis of claim 1 in which the reservoir is a chamber concentric with and located between the pressure chamber and the adjusting chamber.

6. The implant of claim 1 in which the inflating means is connected to the adjusting chamber by a length of tubing.

* * * * *